United States Patent
List et al.

(10) Patent No.: US 8,317,813 B2
(45) Date of Patent: Nov. 27, 2012

(54) DEVICE FOR ACQUIRING A BLOOD SAMPLE

(75) Inventors: Hans List, Hesseneck-Kailbach (DE); Stefan Meinecke, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 353 days.

(21) Appl. No.: 12/627,420

(22) Filed: Nov. 30, 2009

(65) Prior Publication Data
US 2010/0152759 A1    Jun. 17, 2010

(30) Foreign Application Priority Data

Dec. 2, 2008 (EP) .................................. 08170441

(51) Int. Cl.
*A61B 5/151* (2006.01)
(52) U.S. Cl. ........................................................ 606/182
(58) Field of Classification Search .......... 606/181–185, 606/167; 600/573, 583; 604/131, 134
See application file for complete search history.

(56) References Cited

U.S. PATENT DOCUMENTS

| | | | |
|---|---|---|---|
| 4,442,836 A | 4/1984 | Meinecke et al. | |
| 4,924,879 A * | 5/1990 | O'Brien ..................... | 600/583 |
| 5,035,704 A * | 7/1991 | Lambert et al. ............. | 606/182 |
| 5,938,679 A | 8/1999 | Freeman et al. | |
| 6,080,172 A | 6/2000 | Fujiwara | |
| 6,206,901 B1 | 3/2001 | Rutynowski et al. | |
| 6,231,531 B1 | 5/2001 | Lum et al. | |
| 6,409,740 B1 | 6/2002 | Kuhr et al. | |
| 8,118,824 B2 | 2/2012 | Roe | |
| 2005/0131441 A1 | 6/2005 | Iio et al. | |
| 2007/0213682 A1 | 9/2007 | Haar et al. | |
| 2007/0260272 A1 | 11/2007 | Weiss et al. | |
| 2008/0019870 A1 | 1/2008 | Newman et al. | |
| 2008/0262388 A1 | 10/2008 | List et al. | |
| 2008/0269639 A1 | 10/2008 | Korner et al. | |
| 2011/0224712 A1 | 9/2011 | Winheim et al. | |

FOREIGN PATENT DOCUMENTS

| | | |
|---|---|---|
| EP | 0036443 A1 | 9/1981 |
| EP | 1090584 A2 | 4/2001 |
| EP | 1852069 A1 | 11/2007 |
| WO | 2007/073870 A2 | 7/2007 |

* cited by examiner

*Primary Examiner* — Kathleen Sonnett
*Assistant Examiner* — Rachel S Papeika
(74) *Attorney, Agent, or Firm* — Woodard, Emhardt, Moriarty, McNett & Henry LLP

(57) ABSTRACT

A device for acquiring a blood sample comprising a lancet, a puncture drive having a drive rod coupled on the lancet, and a compression spring, which propels it is disclosed. A flywheel mass, which is mounted as to make it movable, is coupled to the drive rod. The flywheel mass can absorb kinetic energy during a propulsion phase and cause retraction of the lancet after reaching a maximum piercing depth. The flywheel mass can be a flywheel connected via a connecting rod to the drive rod and is set into rotation during propulsion of the lancet. After overcoming a dead center defining the maximum piercing depth, rotational energy stored in the flywheel causes the retraction of the lancet. At a specific angle, the rotation of the flywheel is stopped and the residual piercing depth is defined.

14 Claims, 5 Drawing Sheets

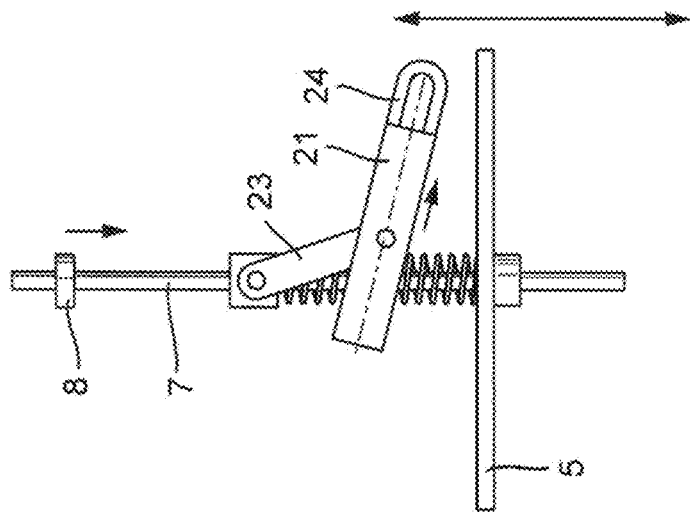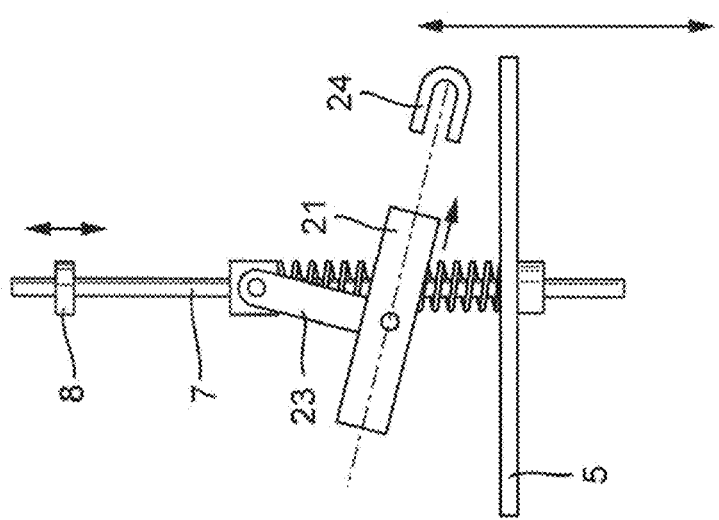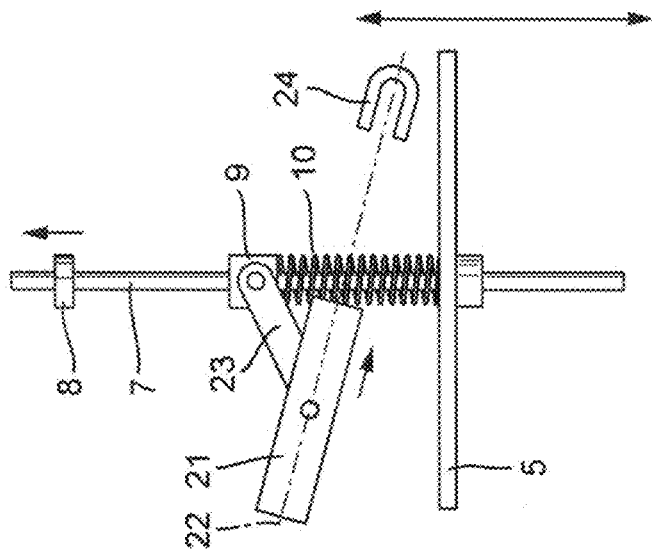

DEVICE FOR ACQUIRING A BLOOD SAMPLE

CROSS-REFERENCE TO RELATED APPLICATIONS

This, application is a continuation of EP 2008/170441, filed Dec. 2, 2008, which is hereby incorporated by reference.

BACKGROUND

The present disclosure generally relates to a device for acquiring a blood sample and, in particular, to a device for acquiring a blood sample, which has a lancet, a puncture drive having drive spring, and a control unit for controlling the rapid piercing and retraction movement of the lancet.

In general, all diabetics need some sort of a device for the regular self-check of the blood sugar level. For this purpose, typically, the tip of a lancet is driven into the skin of a body part, preferably into a fingertip. A small quantity of blood exits from the wound, which is received either directly or by a capillary in the lancet. This blood sample can subsequently be analyzed.

The prior art, in general, is geared toward automatic handheld devices having integrated measuring units and lancets implemented as micro-needles having capillaries, which are implemented as disposables. A supply of disposable lancets is stored in a magazine. The replacement of a used lancet with a new one is performed automatically, so that the user does not have to handle individual parts.

For example, WO 2007/073870 describes a micro-sampler piercing system, whose puncture drive comprises a coiled spring, which propels a pushrod. The head of the pushrod can be coupled to the lancet. The movement of the lancet in the axial direction follows a predetermined movement profile and comprises a propulsion phase, during which the lancet pierces up to a predetermined maximum piercing depth, and a retraction phase immediately following, during which the lancet is retracted up to a predetermined residual piercing depth. Specifically, it has been established that the residual piercing depth is of great significance for optimum sample acquisition and the least possible pain. At the end of the propulsion phase, the pushrod contacts a stop. The drive spring is overstretched, so that the pushrod having the lancet coupled on can also be retracted again during the subsequent retraction phase. Alternatively, the puncture drive comprises a torsion spring, a tension rotor, and a drive rotor driven by the tensioned spring. A control apparatus in the form of a curve controller is used to convert the rotational movement of the drive motor into a linear piercing and retraction movement of a puncture element. A lancet control curve is implemented as a groove in the drive rotor and is followed by a control curve rider, which is connected to the lancet holder.

U.S. Pat. No. 6,206,901 B1 describes a blood sampling device having a lancet, which is driven via a tappet, and a drive spring. The lancet is decoupled from the drive spring for a part of its propulsion phase. In order to retract the lancet from the wound again after the piercing, a second spring is provided. This retraction spring is first tensioned during the propulsion phase, in that kinetic energy of the lancet is stored in the spring and, after reaching the maximum tension of the retraction spring, is returned to the lancet thereby. It is disadvantageous that the lancet is prematurely decelerated by the retraction spring. The entry of the lancet into the skin of the patient is thus slower and more painful.

EP 0 036 443 B1 also describes a lancet device in which the lancet is decoupled from the drive spring during a part of the puncture movement. The retraction of the lancet after the piercing is performed by a second spring, which is tensioned by the lancet during its propulsion movement.

Typically, puncture drives having a drive spring, whose spring force is transmitted linearly in the piercing direction directly to the lancet, have a simple construction and are thus also reliable and cost-effective, and additionally space-saving. They particularly allow installation in a narrow handheld device, which can be handled comfortably and easily by the user. In order to ensure the most rapid possible piercing with the least possible pain, rather strong springs are used. The danger exists that the needle will pierce multiple times due to post-oscillation. For example, in the blood sampling system according to EP 1 852 069 A 1, an oscillation control unit is provided, which acts on the vibratory system made of lancet and drive spring so that multiple piercing is prevented. Three types of action on the oscillation behavior of the lancet are described: on the one hand, a displaceable stop can delimit the oscillation movement of the lancet in the piercing direction. As a second possibility, a damping unit can be provided, for example, in the form of a hydraulic or pneumatic damper. As a further possibility, a location displacement of the drive spring can be provided, by which the zero point of the oscillation of the drive spring is displaced so that even at maximum deflection of the drive spring, further piercing of the lancet is prevented. The oscillation itself is not influenced. In micro-sampler puncture devices, which contain a supply of disposable lancets, in addition to the actual puncture drive, executes short, rapid forward and back movements, a mechanism, which provides comparatively slow, but long actuation strokes, in order to dock the magazined lancets to the puncture drive and release them again after a single use, must also be provided. Therefore, puncture drives, whose control unit works with a control curve, are fundamentally well suitable for alternating rapid and slow movement phases. However, they also have the disadvantage during long strokes that are comparatively large, because otherwise the pitch angles of the control curve grow up to self-inhibition.

If the puncture drive is simply equipped with a mechanical stop which delimits the maximum piercing depth, a hard impact occurs at the moment of the deepest piercing, which not only causes an irritating noise, but also triggers an oscillation of the needle, which results in an increased pain sensation.

The use of a crank drive in a puncture drive is known in the art, see, e.g., U.S. Pat. No. 4,924,879. The drive spring can be implemented therein as a coiled spring and can act directly on a crank wheel, so that it can rotate. The rotation of the crank wheel can then be converted by a pushrod into a linear movement of the lancet. The force flow in the propulsion phase can thus be precisely reversed from the design according to the present disclosure, in which firstly the drive spring can propel the lancet in the piercing direction and the crank drive can be driven passively.

Therefore, there is a need for a device for acquiring a blood sample that has a constructively simple puncture drive with a single drive spring acting in the direction of the movement axis of the lancet that has oscillation-free piercing. There is an additional need for a puncture drive for use in a framework of a slide mechanism to be used for the slow, complete retraction of the lancet, for docking and releasing magazined disposable lancets, and/or for tensioning the drive spring.

SUMMARY

According to the present disclosure, a device for acquiring a blood sample having a movably mounted flywheel mass and a coupling element that couples the flywheel mass to a drive rod and/or the lancet is disclosed. The flywheel mass can be set into motion by the propulsion of the lancet. A part of the kinetic energy of the drive rod and the lancet can be used to accelerate the flywheel mass. If the lancet has reached the reversal point, which defines the maximum piercing depth, the movement energy stored in the flywheel mass can cause the retraction of the lancet. The absorbed kinetic energy can be transmitted back to the drive rod and the coupled-on lancet again. A soft transition from the forward movement into the retraction movement of the lancet may be implemented by the coupled-on flywheel mass and resulting a particularly oscillation-free low-pain piercing.

In accordance with one embodiment of the present disclosure, a coupling gear can be provided, which comprises at least one flywheel mass body movable along a linear movement path and a coupling rod, one end is connected to the drive rod and the other end can be mounted so it can be movable on the flywheel body. The coupling gear can transmit the forward movement of the drive rod having the coupled-on lancet to the flywheel body, which can be set into a translational movement. The coupling gear does not cause the propulsion of the lancet, but rather can be driven passively. The force of the relaxing spring is not only used to drive the lancet, but rather simultaneously also to accelerate the flywheel body. If the lancet travels through the reversal point corresponding to the maximum piercing depth, the inertial mass of the flywheel body can ensure that it still remains in motion. This continued translational movement can be transmitted through the coupling rod to the drive rod and thus initiates the retraction of the lancet. The movement energy stored in the flywheel body can be converted into kinetic energy of the drive rod and the lancet. The coupling gear can control and delimit the piercing depth very precisely.

In accordance with another embodiment of the present disclosure, a crank drive can be provided, which can comprise at least one rotatably mounted flywheel and a connecting rod, one end connected to the drive rod for the lancet and the other end eccentrically mounted on the flywheel. The crank drive can convert the oscillating translational movement of the lancet into a rotational movement of the flywheel, comparable to a crankshaft with connection rod in a piston machine. The crank drive does not cause the propulsion of the lancet, but rather can control and delimit the piercing and retraction movement of the lancet. If the lancet is propelled by the tension force of the drive spring, the flywheel can rotate. Top dead center of the crank drive defines the maximum piercing depth of the lancet. If top dead center is exceeded, the rotational energy stored in the flywheel causes the reversal of the movement direction of the lancet and finally the rapid retraction up to the predetermined residual piercing depth. The velocity profile, using which the lancet is decelerated and retracted again, is decisively a function of the ratio between the inertial mass of the flywheel and the spring force of the drive spring. Fine-tuning of the system is possible in a simple way through a change of the mass of the flywheel.

In accordance with yet another embodiment of the present disclosure, a puncture drive, including compression spring and the crank drive, comprising at least one flywheel, can be situated jointly on a sliding carriage, which is displaceable parallel to the movement axis of the lancet. Specifically, if the puncture drive is blocked after reaching the residual piercing depth, the drive rod becomes a component which is no longer movable relative to the sliding carriage. The sliding carriage can then execute the long-stroke and slow movements which can be used for the complete retraction of the lancet and can be transmitted via the blocked drive rod to the lancet. The sliding carriage can advantageously also be used for tensioning the puncture drive, in that a tensioning stop on a flywheel can be moved against a fixed counter stop.

In accordance with still yet another embodiment of the present disclosure, a drive spring can be a coiled spring, such as a compression spring situated coaxially around the drive rod, a plunger can be provided on the drive rod, against which the compression spring presses, and the connecting rod of the crank drive can be connected via the plunger to the drive rod. The plunger can have two functions: 1) it can form contact surface for the compression spring and can transmit its spring force to the drive rod, and 2) it can form a bearing block for the upper pivot bearing of the connecting rod. The plunger can be dimensioned so that it protrudes laterally beyond the compression spring, so that the connecting rod can have sufficient spacing to the compression spring in all movement phases. The connecting rod can thus be relatively short, so that the puncture drive can remain compact. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 4a illustrates a schematic view of a fourth embodiment for acquiring a blood sample, having a coupling gear and diagonal movement path of the flywheel body during the propulsion phase of the lancet.

FIG. 4b illustrates the device from FIG. 4a at maximum piercing depth according to an embodiment of the present disclosure.

FIG. 4c illustrates the device from FIG. 4a at residual piercing depth according to an embodiment of the present disclosure.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Figure 1C:
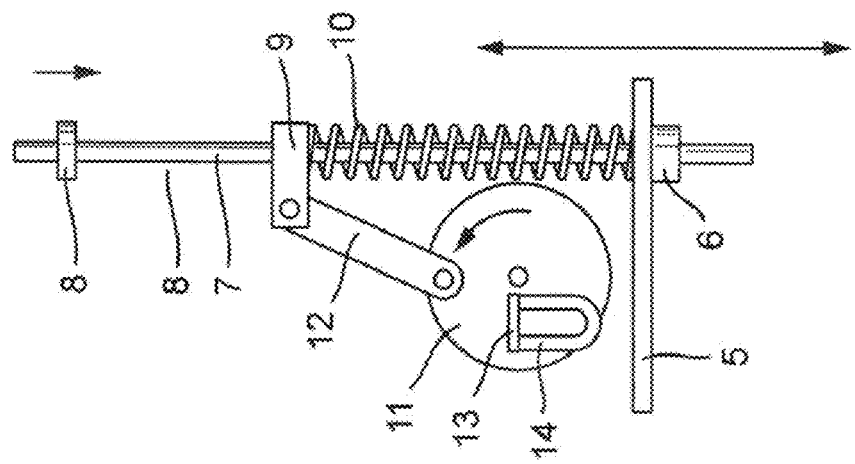
FIG. 1c illustrates the device from FIG. 1a at residual piercing depth according to an embodiment of the present disclosure.
Figure 1B:
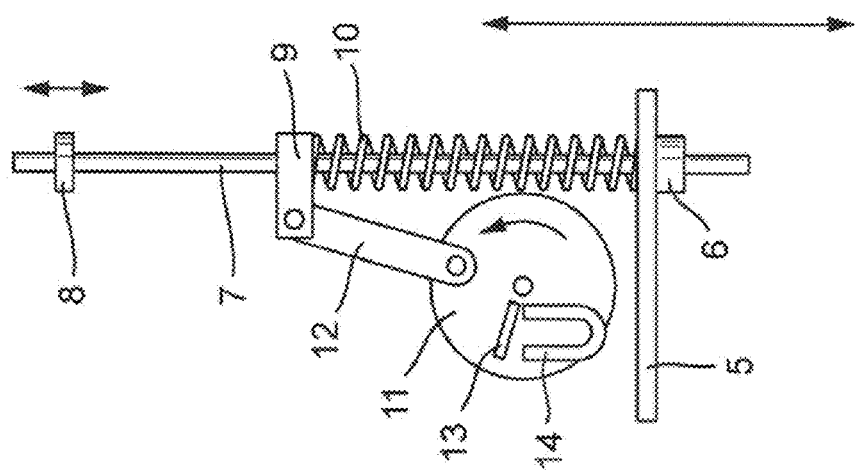
FIG. 1b illustrates the device from FIG. 1a at maximum piercing depth according to an embodiment of the present disclosure.
Figure 1A:
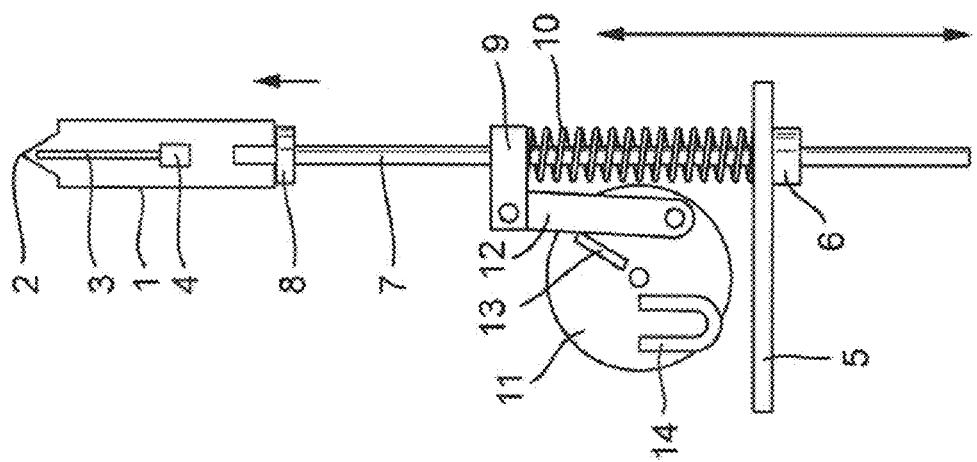
FIG. 1a illustrates a schematic view of a first embodiment for acquiring a blood sample having a crank drive and a flywheel during the propulsion phase of the lancet.

Referring initially to FIGS. 1a-c, elements of the drive mechanism of a device for acquiring a blood sample using a lancet 1 is illustrated. The lancet 1 can pierce into the skin of a body part and can subsequently and immediately, partially retract in order to receive the blood exiting from the wound in the skin. The lancet 1 can be a disposable article and can comprise a piercing tip 2, a capillary channel 3, and a small blood collection chamber 4.

A puncture drive can be mounted on a sliding carriage 5, which can execute large slow movements for the engagement and disengagement of the lancet—indicated by the long double arrow—in order to replace the lancet 1 with a new exemplar after a single use.

The sliding carriage 5 can carry a friction bearing 6, in which a round drive rod 7 can be mounted so it can be displaceable in the axial direction so that the drive rod 7 can penetrate the sliding carriage 5. On its upper end, the drive rod 7 can have a coupling 8 to removably couple the lancet 1 on the drive rod 7. A plunger 9 can be mounted fixed at some distance below the coupling 8 on the drive rod 7. A compression spring 10 can be situated coaxially around the drive rod 7 such that the lower end can press against the sliding carriage 5. In one exemplary embodiment, the compression spring 10 can be a cylindrical coiled spring made of steel having a linear spring characteristic. The upper end of the compression spring 10 can press against the bottom side of the plunger 9, so that it can propel the drive rod 7 and the coupled-on lancet 1 in the direction of the small arrow. The movement axis of the drive rod 7 having the lancet 1 and the movement direction of the sliding carriage 5 can be parallel to one another. The compression spring 10 can already be no longer completely tensioned in FIG. 1a, i.e., the lancet can be in the rapid propulsion phase.

The sliding carriage 5 can simultaneously also be used for the purpose of tensioning the puncture drive, for example, the tappet to drive the lancet 1 forward can be moved against a stop mounted fixed in a housing until the drive spring is tensioned and is engaged in the trigger mechanism. Such so-called "ballistic" drives have not offered any possibility until now of assuming a defined position, which corresponds to the residual piercing depth, rapidly and without post-oscillation after reaching the maximum piercing depth.

A flywheel 11 can be mounted so that it can rotate transversely to the movement axis of the lancet 1 laterally adjacent to the drive rod 7. A connecting rod 12 can be mounted at one end so it can be rotatable in the area of the edge of the flywheel 11, while the other end of the connecting rod 12 can be mounted so it can be rotatable on the plunger 9. The plunger 9 can protrude laterally far enough away so that the connecting rod 12 does not come into contact with the turns of the compression spring 10. The flywheel 11 can carry a driven stop element 13, which can still be at a relatively large distance from the associated counter stop 14, which can be mounted fixed on the sliding carriage 5, in FIG. 1a.

Flywheel 11 and connecting rod 12 can form a passive driven crank drive, which can convert the translational movement of the drive rod 7 into a rotational movement of the flywheel 11. A part of the kinetic energy of the drive rod 7 and the coupled-on lancet 1 can be converted into rotational energy of the flywheel 11.

In FIG. 1b, the lancet 1 has reached the maximum piercing depth. The crank drive can be at top dead center and the compression spring 10 can be maximally deflected. In one embodiment, the flywheel 11 has rotated approximately 90° counterclockwise. The stop element 13 can be shortly in front of the counter stop 14.

In FIG. 1c, the top dead center has been overcome. The rotational energy stored in the flywheel 11 can cause the retraction of the lancet 1, against the tension force of the compression spring 10, which can already become somewhat shorter. Rotational energy of the flywheel 11 can thus transmitted back to the drive rod 7 and can be converted into potential energy of the compression spring 10. The rotational movement of the flywheel 11 can be stopped at the end in that the stop element 13 has arrived at the counter stop 14. The linear movement of the drive rod 7 and the coupled-on lancet 1 can be thus also initially decelerated and finally can be stopped in a position which corresponds to the predetermined residual piercing depth.

The proposed crank drive, comprising flywheel 11 and connecting rod 12 connected to the lancet 1, can force a reversal of the movement direction of the lancet 1 at top dead center independently of whether the drive spring is already completely relaxed or is even overstretched at this moment. However, in one embodiment, the retraction can be performed against the action of the drive spring, which cannot yet be completely relaxed. The spring force can be converted into rotation energy somewhat earlier, but due to the retraction movement of the lancet 1 against a certain residual tension force of the compression spring, the danger of an oscillation, which would be particularly annoying in the area of the maximum piercing depth, can reliably be avoided.

The crank drive can be situated laterally offset to the piercing axis of the lancet 1. The rotational bearings of the connecting rod 12, which can be situated eccentrically, in the area of the outer edge of the flywheel 11, thus can move along a circular arc, so that the lateral spacing to the movement axis of the lancet 1 can change during the forward and reverse movement of the lancet 1. The greater the spacing and thus the angle at which the connecting rod 12 engages on the drive rod 7, the slower the flywheel 11 can rotate. This can have the result that at the beginning of the propulsion phase, the flywheel 11 can only be accelerated moderately, but shortly before reaching top dead center it can accelerate very strongly. After the reversal point of the lancet 1, the inertial mass of the flywheel 11 can ensure that it can rotate further. The coupled-on crank drive having flywheel 11 thus initially can ensure strong deceleration of the lancet 1 shortly before reaching the maximum piercing depth and subsequently can cause the rapid retraction up to the residual piercing depth. The crank drive can simultaneously define and delimit the piercing depth.

In other words, after the retraction phase, the lancet 1 can be fixed as rapidly as possible in the position which can correspond to the predetermined residual piercing depth. This can be performed most simply by a stop element 13 which can rotate with the flywheel 11 and can hit a fixed counter stop element 14 at a predetermined angle. The rotational movement of the flywheel can thus be stopped at the end of the retraction phase and the residual piercing depth can be defined.

In order that the lancet 1 can also no longer move forward after reaching the residual piercing depth, which would result in a further painful piercing, it can be expedient to fix the stop element 13 on the counter stop element 14. In one exemplary embodiment, the counter stop element 14 can be implemented as a permanent magnet, whose poles can be closed by the stop element 13, which can be a magnetic armature. In the terminal position, stop element 13 and counter stop 14 can thus be held against one another by magnetic force. The puncture drive can thus be fixed. Back oscillation of the lancet 1 with the danger of further piercing can thus be prevented.

Figure 2A:
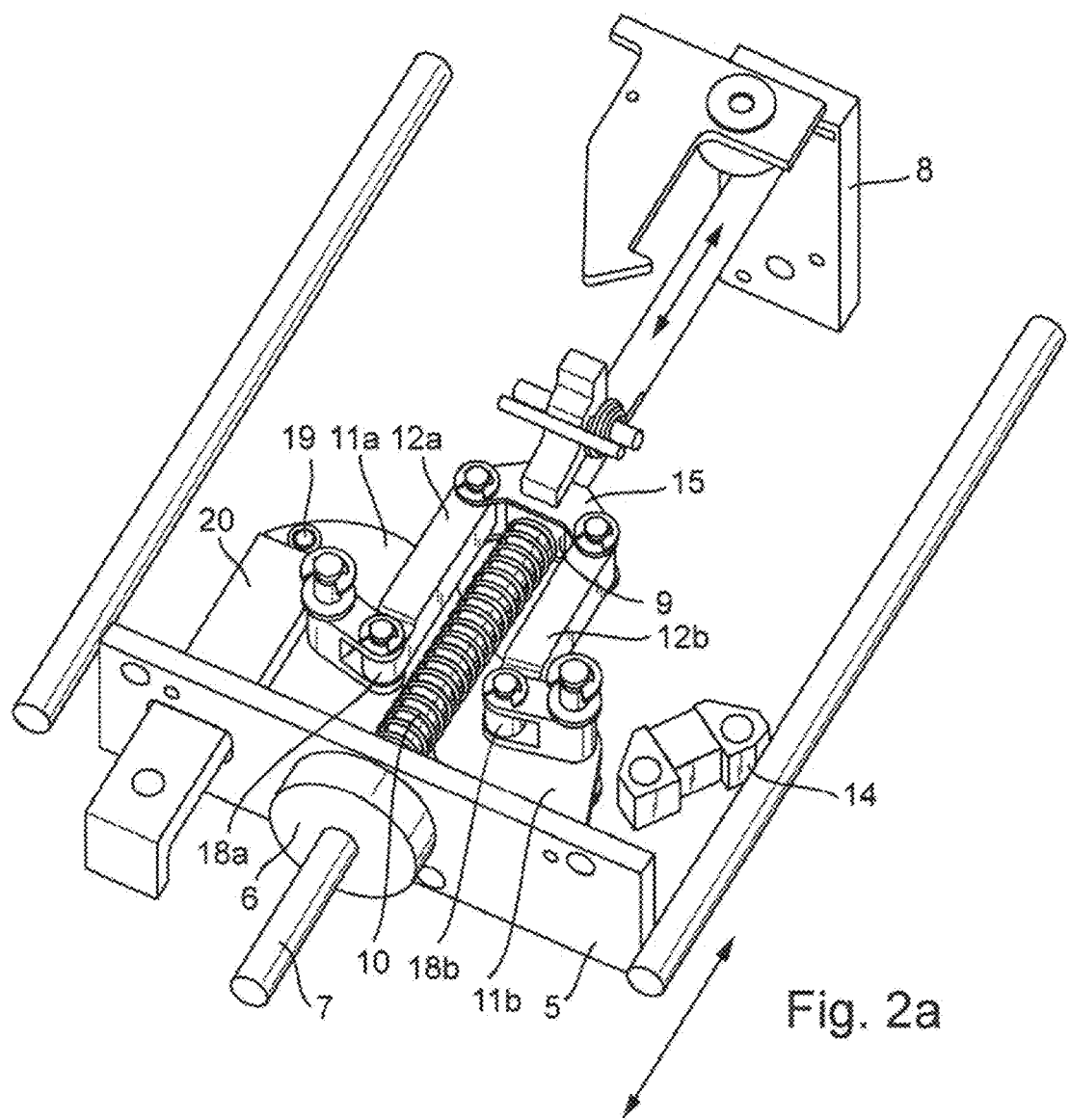
FIG. 2a illustrates, in an above perspective view, a second embodiment for acquiring a blood sample, having two symmetrical crank drives and two flywheels.
Figure 2B:
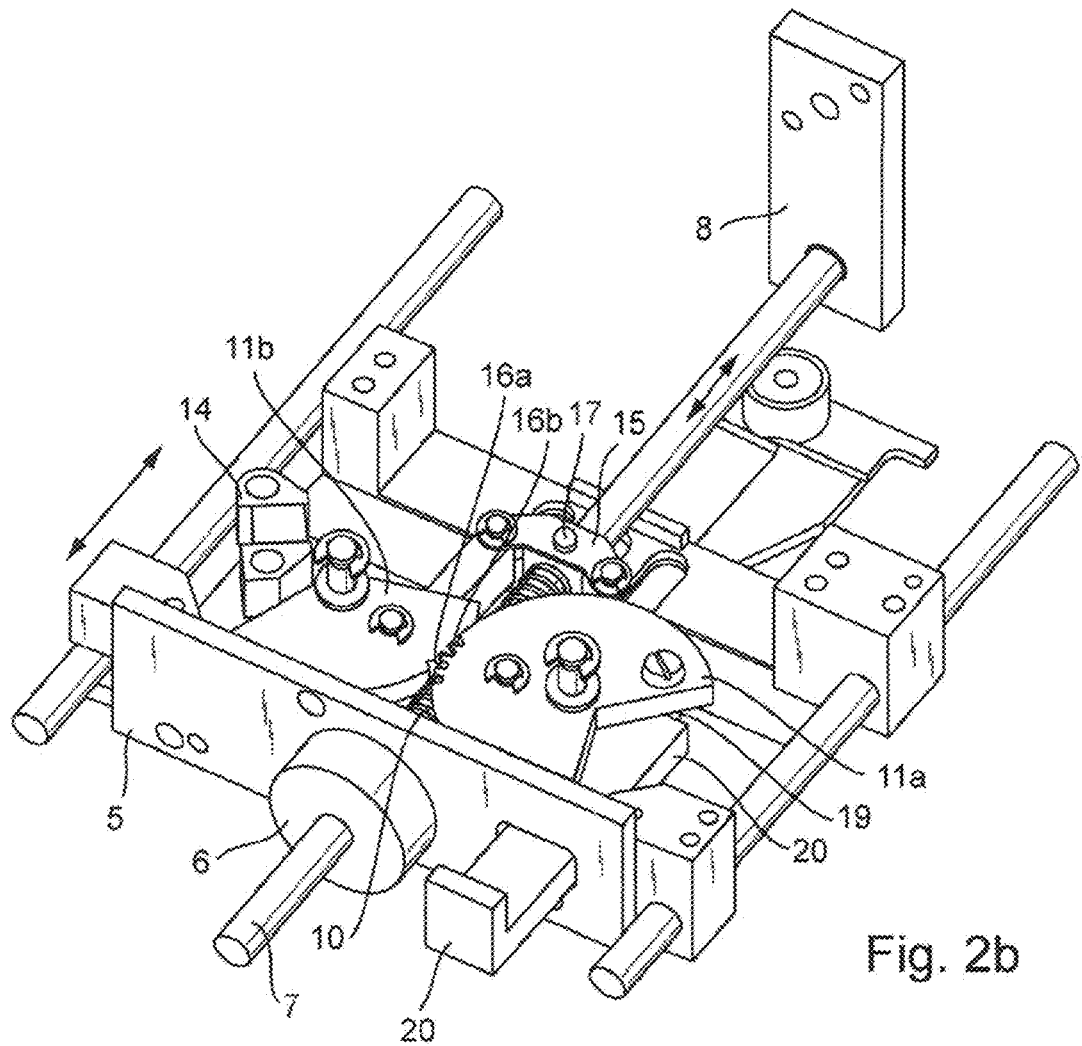
FIG. 2b illustrates the device from FIG. 2a, seen from below, according to an embodiment of the present disclosure.

The puncture drive embodiment in FIGS. 2a and 2b can comprise two flywheels 11a, 11b situated symmetrically on both sides of the drive rod 7. The plunger 9 can carry a transverse yoke 15, whose two opposing ends can each be connected by a connecting rod 12a and 12b of the flywheels 11a and 11b, respectively. The flywheels 11a, 11b can have gearings 16a, 16b on their front faces, which can engage in one another. The two flywheels 11a, 11b can thus be positively synchronized with one another. The transverse yoke 15 can be mounted so it can be pivotable using a pivot joint 17 giving the mechanical system the required degree of freedom in order to also run without obstruction in the event of a possible tilt of the drive rods 7.

In other words, in the event of a lateral offset between rotational axis of the flywheel 11 and piercing axis of the lancet 1, lateral forces can unavoidably act on the drive rod 7. Annoying friction can thus occur in the guide bearings. It can therefore be advantageous to construct the crank drive symmetrically, i.e., to situate two flywheels 11a.11b opposite to one another on both sides of the drive rod 7. The plunger 9 on the drive rod 7 can then comprise a transverse yoke 15, so that the two opposing ends of the transverse yoke 15 can be connectable by one connecting rod 12a, 12b each to the flywheels 11a, 11b. The lateral forces transmitted by the connecting rods 12a, 12b via the plunger 9 to the drive rod 7 can cancel out in this symmetrical configuration.

As can be seen in FIG. 2a, the flywheels 11a, 11b can be implemented like simple crankshafts, having a single crank cheek and one crank pin 18a or 18b each, on which the connecting rods 12a, 12b can be mounted like conrods.

If the flywheels 11a, 11b are located in their terminal position corresponding to the residual piercing depth, they can be blocked by the adhesion to one another of stop element 13 and counter stop 14 (cf. FIG. 1c). The drive rod 7 can thus also be fixed rigidly on the sliding carriage 5. A displacement of the sliding carriage 5 downward in the direction of the two arrows can thus be transmitted to the drive rod 7. In this way, not only can the slow retraction of the lancet be executed beyond the residual piercing depth, but also the long-stroke movements for the coupling and decoupling of the lancet.

A tension stop 19 can be provided on the edge on the left flywheel 11a in FIG. 2a. When the sliding carriage 5 moves opposite to the propulsion direction of the lancet 1, the tension stop 19 can hit a tension counter stop 20 mounted on the device housing outside the sliding carriage 5. The flywheel 11a can thus be rotated back, the retention force between stop element 13 and counter stop 14 being overcome. The compression spring 10 may be tensioned in this way.

The two crank drives and in particular the flywheels 11a, 11b can be synchronized with one another, for example, in that the two flywheels 11a, 11b can have gearings engaging in one another on their front sides. In order to prevent jamming of the two crank drives, it can be expedient to connect the two mirror-symmetrical connecting rods 12a, 12b to the drive rod 7 via a further pivot joint. This can be performed by a transverse yoke 15, which can be mounted on the drive rod 7 so it can be pivoted. Because only very small pivot movements occur here, the required mobility can be produced by a film hinge, for example, whereby the manufacturing expense can be kept extremely low.

Figure 3A:
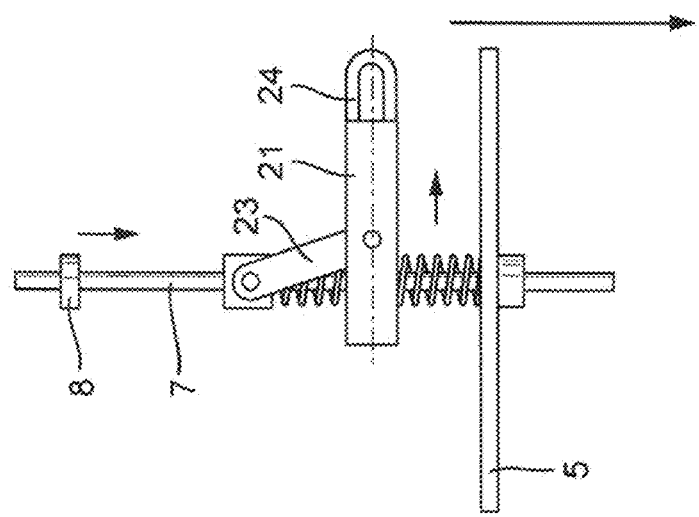
FIG. 3a illustrates a schematic view of a third embodiment for acquiring a blood sample having a coupling gear and flywheel bodies during the propulsion phase of the lancet.
Figure 3B:
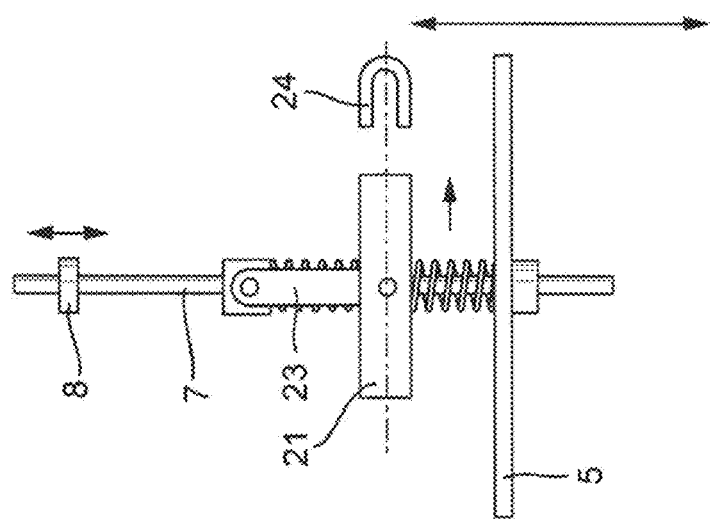
FIG. 3b illustrates the device from FIG. 3a at maximum piercing depth according to an embodiment of the present disclosure.
Figure 3C:
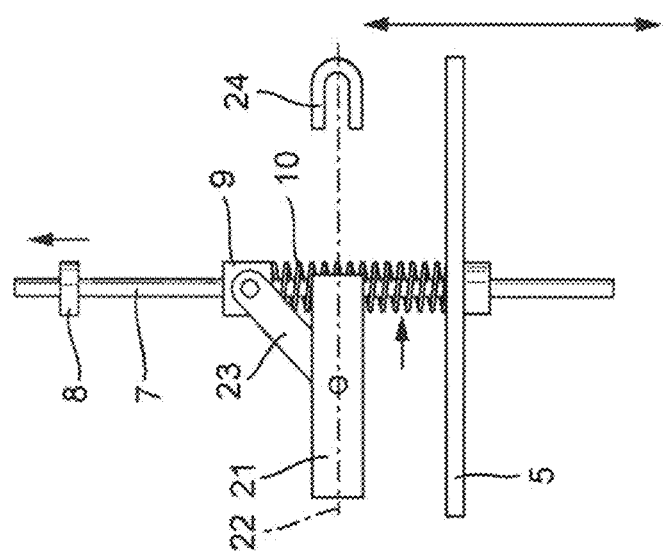
FIG. 3c illustrates the device from FIG. 3a at residual piercing depth according to an embodiment of the present disclosure.

The schematic images of FIGS. 3a-c show another embodiment of the drive mechanism. The drive rod 7 can carry a plunger 9. A compression spring 10 can press against the bottom of the plunger 9 so that the drive rod 7 can be propelled in the direction of the small arrow. The puncture drive can be seated on the sliding carriage 5, which can be displaceable relatively slowly in the direction of the large arrow.

A cuboid flywheel mass body 21 can be mounted so it can be displaceable along a linear movement path 22. A coupling rod 23 can be mounted at its lower end so it can be rotatable on the flywheel body 21, precisely in the center. The upper end of the coupling rod 23 can be mounted so it can be rotatable on the plunger 9. Flywheel body 21 and coupling rod 23 can form a passive driven coupling gear, which can convert the forward and back movement of the drive rod 7 into a lateral movement of the flywheel body 21 and vice versa. The movement path 22 can run transversely to the piercing axis. The propulsion phase has just begun in FIG. 3a.

In FIG. 3b, the drive rod 7 has reached its reversal point, which can correspond to the maximum piercing depth. The coupling rod 23 can be vertical. The coupling gear can be at dead center. The compression spring 10 can be maximally deflected. The flywheel body 21 can have maximum velocity. Because of its inertial mass, the flywheel body 21 can move further in the direction of the transverse arrow transversely to the piercing axis. The right end of the flywheel body can approach a delimitation element mounted fixedly on the sliding carriage 5.

The rapid retraction phase can have just ended in FIG. 3c. The compression spring 10 can already be somewhat compressed again. The movement energy of the flywheel body 21 can be displaced back to the drive rod 7 and the lancet can be coupled thereon (see FIG. 1a). The puncture drive can be stopped at the end, in that the right front face of the flywheel body 21 can hit the delimitation element 24.

In one exemplary embodiment, the flywheel body 21 can be produced from ferromagnetic iron. The delimitation element 24 can be implemented as a permanent magnet, whose poles can be closed by the flywheel body 21 acting as a magnetic armature. In the terminal position, the flywheel body 21 and the delimitation element 24 can thus be held on one another by magnetic force. The puncture drive can thus be fixed.

The movement path 22 of the flywheel body 21 can run substantially transversely to the piercing axis of the lancet 1. The movement path 22 can be a straight line. Because the flywheel body 21 can move substantially transversely to the piercing axis, the path of the drive rod 7 and the lancet 1 can be delimited in the propulsion direction. From the reversal point, any further movement of the flywheel body 21 necessarily can have the result of the drive rod 7 and the lancet 1 can be moved back downward again. The kinematics may be used to apply a transition from the forward movement to the reverse movement with predetermined velocity profile to the piercing movement of the lancet 1. The velocity profile, using the lancet 1 decelerated at the end of the forward movement and subsequently and immediately, partially retracted, can be a function of the ratio between the inertial mass of the flywheel body 21 and a spring force of the drive spring. Fine-tuning of the system can be possible by changing the mass of the flywheel body 11.

If the movement path 22 of the flywheel body 21 does not run perpendicularly to the piercing axis, the bearing point of the coupling rod 23 on the flywheel body 21 can execute a movement which can have a component parallel to the piercing direction. The movement component acting parallel to the piercing axis can be added to the forward and/or reverse movement of the lancet 1. The ratio of the kinetic energies which can be transmitted from the drive rod 7 to the flywheel body 21 and vice versa may be varied. The angle at which the movement path of the flywheel body 21 can run diagonally relative to the piercing axis can be expediently between about 5° and about 45°.

If the flywheel body 21 does not move along a straight line, but instead its movement path is curved, further degrees of freedom can be provided, in order to design the velocity and/or acceleration profile of the lancet 1 optimally, especially in the area of the maximum piercing depth.

In relation to puncture drives in which the propulsion of the lancet 1 is delimited by a hard stop or a second spring takes over the retraction movement, top dead center can be activated by the conversion of a circular movement into a translational movement, which can automatically result in a non-linear characteristic, i.e., in a soft but precisely controlled movement sequence.

The flywheel 11 can be mounted so it can be rotatable transversely to the piercing axis of the lancet 1, so that the rotational axis of the flywheel 11 and the piercing axis of the lancet 1 can be substantially perpendicular to one another. Instead of such a typical crank drive, however, a configuration can also be used in which the rotational axis of the flywheel 11 can run substantially parallel to the piercing axis of the lancet. In particular, installation space can thus be saved with a very light embodiment of the drive rod 7.

The further embodiment according to FIGS. 4a, 4b, and 4c only differs from the previously described embodiment in that the movement path 22 of the flywheel body 21 does not run transversely, but rather diagonally by approximately 15° relative to the piercing axis. The coupling rod 23 is thus not vertical at top dead center, but rather can stand diagonally to the left by the same angle, as shown in FIG. 4b. Because the center point of the flywheel body 21, which simultaneously forms the linkage point for the coupling rod 23, can move on a diagonal path downward, less kinetic energy can be required in order to accelerate the flywheel body 21.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for acquiring a blood sample, the device comprising:
   a lancet for piercing into skin of a body part in a controlled forward and back movement and for subsequently and immediately, partially retracting in order to receive blood exiting from the piercing;
   a puncture drive comprising a drive rod coupled to the lancet and a drive spring acting in a direction of a piercing axis of the lancet, wherein the drive spring is situated coaxially around the drive rod;
   a control unit for controlling the piercing and retraction of the lancet according to a predetermined movement profile comprising at least one rapid propulsion phase, in which the lancet pierces up to a predetermined maximum piercing depth, and a rapid retraction phase, in which the lancet is partially retracted to a predetermined residual piercing depth;
   a rotatable mounted flywheel, wherein a rotational axis of the flywheel is laterally offset from the piercing axis of the lancet; and
   a coupling element for coupling the flywheel to the drive rod in such a manner that the propulsion phase of the lancet sets the flywheel into motion and, after reaching the maximum piercing depth, movement energy stored in the flywheel causes the retraction of the lancet.

2. The device according to claim 1, wherein a movement path of the flywheel is curved and substantially circular.

3. The device according to claim 1, further comprising,
   a crank drive comprising the flywheel and a connecting rod, wherein one end of the connecting rod is connected to the drive rod and the other end is mounted eccentrically on the flywheel, so that the propulsion of the lancet sets the flywheel into rotation and, after overcoming top dead center, which defines the maximum piercing depth, the rotational energy stored in the flywheel causes the retraction of the lancet.

4. The device according to claim 3, wherein a rotational axis of the flywheel is situated substantially transversely to the piercing axis of the lancet.

5. The device according to claim 3, wherein the retraction of the lancet occurs against a tension force of a compression spring.

6. The device according to claim 3, wherein the drive spring is a compression spring, a plunger is provided on the drive rod against which the compression spring presses, and the connecting rod is connected via the plunger to the drive rod.

7. The device according to claim 3, wherein the flywheel has a driven stop element, which hits a fixed counter stop at a predetermined angle to stop rotational movement of the flywheel defining the residual piercing depth.

8. The device according to claim 7, wherein the stop element adheres magnetically to the counter stop, in order to fix the puncture drive.

9. The device according to claim 3, wherein two flywheels are arranged opposite to one another on both sides of the drive rod, wherein a transverse yoke is situated on the drive rod, and wherein two opposing ends of the transverse yoke are each connected by a crankshaft to the flywheels.

10. The device according to claim 9, wherein the transverse yoke is pivotally mounted.

11. The device according to claim 9, wherein the two flywheels are synchronized with one another.

12. The device according to claim 11, wherein the two flywheels have gearings on front faces of the flywheels such that the gearings engage each other.

13. The device according to claim 3, wherein the puncture drive and the crank drive are arranged on a sliding carriage, which is displaceable parallel to the piercing axis of the lancet.

14. The device according to claim 13, wherein a tension stop is seated on at least one flywheel of the crank drive, which hits a tension counter stop as a result of a displacement of the sliding carriage opposite to a propulsion direction of the lancet, whereby the flywheel is rotated back in order to tension the compression spring.

* * * * *